(12) United States Patent
Imaizumi et al.

(10) Patent No.: US 6,410,287 B1
(45) Date of Patent: Jun. 25, 2002

(54) ENZYME PARTICLES

(75) Inventors: Yoshinobu Imaizumi; Koichi Ohori; Itsuro Tsukahara; Hiroyuki Yamashita, all of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/581,137

(22) PCT Filed: Oct. 8, 1999

(86) PCT No.: PCT/JP99/05555

§ 371 (c)(1),
(2), (4) Date: Jun. 9, 2000

(87) PCT Pub. No.: WO00/22104

PCT Pub. Date: Apr. 20, 2000

(30) Foreign Application Priority Data

Oct. 9, 1998 (JP) .......................................... 10-287667
Jun. 15, 1999 (JP) .......................................... 11-167840

(51) Int. Cl.⁷ .............................. C12N 9/98; C12N 11/16; C12N 11/04; C11D 1/00; C11D 3/40
(52) U.S. Cl. .................. 435/187; 435/174; 435/182; 510/114
(58) Field of Search ................................ 435/187, 174, 435/182; 510/114

(56) References Cited

U.S. PATENT DOCUMENTS

| 4,869,843 A | * | 9/1989 | Saito et al. ............... 252/135 |
| 5,376,288 A | | 12/1994 | Falholt et al. |
| 5,851,975 A | | 12/1998 | Kiuchi et al. |

FOREIGN PATENT DOCUMENTS

| GB | 1294557 | 8/1970 |
| JP | 473734 | 2/1972 |
| JP | 5022506 | 7/1975 |
| JP | 60037983 | 2/1985 |
| JP | 62257990 | 11/1987 |
| JP | 2097388 | 4/1990 |
| JP | 7289259 | 11/1995 |
| JP | 10023888 | 1/1998 |
| JP | 10204494 | 8/1998 |
| WO | Wo-90/15856 | * 12/1990 |
| WO | 9015856 A1 | 12/1990 |
| WO | 9638527 A1 | 12/1996 |
| WO | 981544 A1 | 1/1998 |

* cited by examiner

Primary Examiner—David M. Naff
Assistant Examiner—K. C. Srivastara
(74) Attorney, Agent, or Firm—Birch, Stewart, Kolasch & Birch, LLP

(57) ABSTRACT

Enzyme granules are provided in which an enzyme is rapidly eluted, without insoluble remnants, and generation of powdery dust is suppressed, and which granules have a property such that classification phenomenon generated among the granules in a detergent composition is less likely to take place, in a case where the enzyme granules are formulated together with other components in a detergent. The enzyme granule comprise (A) water-insoluble substance and or a slightly water-soluble substance; (B) a water-soluble binder; and (C) an enzyme. A dye may also be present for coloring. The content of (A) component is 45% by weight or more, and the enzyme granules have an average particle size of from 150 to 500 μm and a bulk density of from 500 to 1,000 g/L, and have a structure such that more amount of (B) component is present near the surface of the enzyme granules than in the inner portion thereof. The enzyme granule may be aggregated to form an enzyme granule aggregate. A process is provided for preparing the enzyme granule by spray-drying a slurry containing (A), (B) and (C). The enzyme granule aggregate may be prepared by adding an aqueous binding solution to the granules and drying, or by adding molten thermoplastic binder to the granules and cooling.

7 Claims, 3 Drawing Sheets

ENZYME PARTICLES

This application is the national phase under 35 U.S.C. § 371 of PCT International Application No. PCT/JP99/05555 which has an International filing date of Oct. 8, 1999, which designated the United States of America.

TECHNICAL FIELD

The present invention relates to enzyme granules suitably formulated in a detergent. Further, the present invention relates to a process for preparing the enzyme granules. Further, the present invention relates to an enzyme granule aggregate suitably formulated in a detergent and a process for preparing the same.

BACKGROUND ART

In many cases, various enzymes are formulated in detergents such as laundry powder detergents, powder bleaching agents and powder detergents for automatic dishwashing machines for the purpose of enhancing their detergency.

Since an enzyme exhibits its effects for the first time after dissolving in water, the enzyme has such a property that a certain amount of time is required before exhibiting its effect. Therefore, in order to optimally exhibit the performance of the enzyme, whether or not the enzyme granules have a property of quickly eluting an enzyme from enzyme granules (referred to as "fast dissolubility") is important. Especially regarding the laundry detergents, and the like, its importance is even more increasing under the present situation of the tendency of shortened washing time.

Further, in a case where the formulation to a detergent is considered, when there are insoluble remnants of the enzyme granules at the termination of washing, there arises a problem such as deposition of the insoluble remnant components to washing items. Therefore, it is important that all of the substances constituting the enzyme granules are dispersed within a washing period, thereby preventing to have insoluble remnants.

In addition, in order to secure safety of the working environment, it is important to suppress the amount of powdery dusts generated from the enzyme granules (referred to as "amount of dusts generated").

Further, in a case where after-blending to the detergent is considered, it is desired that the enzyme granules are homogeneously distributed in the detergent from the viewpoint of quality. In order to achieve this, it is important to prevent the classification of the enzyme granules with other granules constituting the detergent by approximating the particle size and the bulk density of the enzyme granules to those of the other granules. In addition, in consideration of external appearance, the larger the particle size, the more desirable, from the viewpoint of the visual confirmability, and the lower the bulk density, the more desirable, from the viewpoint of the number of granules.

In consideration of these viewpoints, there is becoming increasingly important a technique satisfying the fast dissolubility and the low dust generating property, properties required regardless of being formulated in a detergent composition, and also being capable of controlling a particle size and a bulk density, properties becoming important when formulated in a detergent, to match those of the detergent.

However, these properties are closely related to each other. For instance, while the dissolubility is improved by making the particle size small, the amount of dusts generated tends to increase at the same time. While the amount of dusts generated is lowered by increasing the bulk density, the dissolubility tends to be lowered at the same time. Therefore, it has been conventionally difficult to obtain enzyme granules satisfying these required properties at the same time.

For instance, Japanese Examined Patent Publication No. Sho 50-22506 discloses a process for preparing a microcapsule comprising an enzyme for detergents, comprising spray-drying a solution comprising the enzyme for detergents and an inorganic salt being copresent in a water-soluble binder solution, or a dispersion thereof. While the microcapsule actually prepared which has a particle size in a range of from 20 to 130 $\mu$m can be thought to satisfy excellent dissolubility when formulated in a detergent to be used, it is difficult to suppress the classification phenomenon caused among the granules, because the particle size is extremely small as compared to the detergent. In addition, in the enzyme granules obtainable by this technique, since the content of the water-soluble substance is substantially large, the enzyme granules have a hollow structure having a weak strength, so that it is difficult to suppress the amount of dusts generated, and thereby the required properties described above for an enzyme could not be satisfied at the same time.

Japanese Patent Laid-Open No. Hei 7-289259 discloses a process for preparing enzyme granules for detergents, comprising subjecting a mixture comprising an enzyme for detergents and aluminosilicate powder to agitation and tumbling granulation using a water-soluble organic binder. According to this process, a problem regarding the suppression of the amount of dusts generated is solved by carrying out granulation. However, it is difficult to satisfy the fast dissolubility owing to an increase in the particle size and the compression of the granules during granulation, and thereby the required properties described above for an enzyme could not be satisfied at the same time even by this process.

An object of the present invention is to provide enzyme granules in which an enzyme is rapidly eluted, without insoluble remnants, and the generation of the powdery dusts is suppressed, thereby having a property such that classification phenomenon generated among the granules in the detergent composition is less likely to take place (referred to as "non-classifiable property"), in a case where the enzyme granules are formulated in a detergent together with other components. A further object of the present invention is to provide a process for preparing the enzyme granules. A still another object is to provide an enzyme granule aggregate in which an enzyme is rapidly eluted, without insoluble remnants, and the generation of the powdery dusts is suppressed, thereby having a non-classifiable property, in a case where the enzyme granules are formulated in a detergent together with other components, by aggregating enzyme granules having structure such that more amount of a water-soluble binder is present near the surface of the enzyme granules than the inner portion thereof. A still another object is to provide a process capable of suitably preparing an enzyme granule aggregate. These objects and other objects of the present invention will be apparent from the following description.

DISCLOSURE OF INVENTION

Specifically, the present invention relates to:

[1] enzyme granules comprising (A) a water-insoluble substance and/or a slightly water-soluble substance; (B) a water-soluble binder; and (C) an enzyme, wherein the content of (A) component is 45% by weight or more, and wherein the enzyme granules have an average particle size of from 150 to 500 $\mu$m and a bulk density of from 500 to 1,000 g/L, and have a structure such that more amount of (B) component is present near the surface of the enzyme granules than in the inner portion thereof;

[2] a process for preparing the enzyme granules of item [1], comprising spray-drying a slurry comprising (A) a water-insoluble substance and/or a slightly water-soluble substance; (B) a water-soluble binder; and (C) an enzyme at a temperature so as not to substantially deactivate the enzyme, to give the enzyme granules;

[3] an enzyme granule aggregate comprising enzyme granules comprising (A) a water-insoluble substance and/or a slightly water-soluble substance; (B) a water-soluble binder; and (C) an enzyme, wherein the enzyme granules have a structure such that more amount of (B) component is present near the surface of the enzyme granules than in the inner portion thereof; and

[4] a process for preparing an enzyme granule aggregate, comprising adding water or an aqueous binder solution to enzyme granules, drying and/or cooling the resulting mixture, the enzyme granules comprising (A) a water-insoluble substance and/or a slightly water-soluble substance; (B) a water-soluble binder; and (C) an enzyme, wherein the enzyme granules have a structure such that more amount of (B) component is present near the surface of the enzyme granules than in the inner portion thereof; or comprising adding a molten thermoplastic binder to the enzyme granules and cooling the resulting mixture, thereby giving the enzyme granule aggregate.

Figure 1:
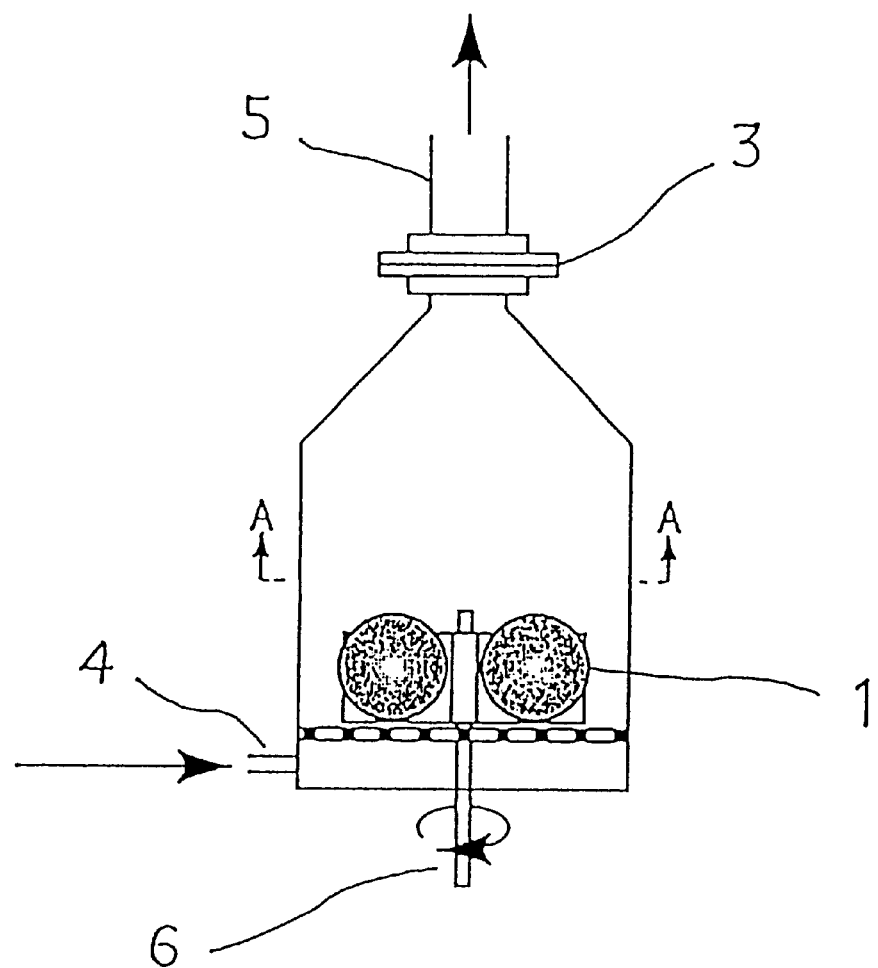
FIG. 1 is a schematic view showing the construction of a rotatable dustmeter used for determination of the amount of dusts generated in the present invention. An upper view of FIG. 1 is a front view, and a lower view is a cross-sectional view taken along the line A—A, respectively. 1 is a pulverizing ball, 3 is a filter, 4 is an inlet for introducing air, 5 is an outlet for discharging air, and 6 is a rotatable shaft, respectively.
Figure 1:
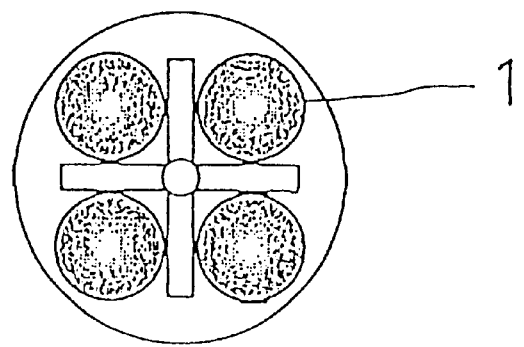

BEST MODE FOR CARRYING OUT THE INVENTION 1. (A) Component

The water-insoluble substance or water slightly soluble substance of (A) component usable in the present invention is not particularly limited, as long as the substance does not exhibit dissolubility in water, or slightly exhibit dissolubility, the substance capable of exhibiting properties of having substantially no deactivation of an enzyme, being unreactive with a water-soluble binder, and being dispersible in water. The substance may be an inorganic substance or organic substance, and the inorganic substance is more preferable, from the viewpoint that the higher the stability against heat, the more advantageous, in a case where a process requiring heat, such as spray-drying, is employed. Concrete examples of (A) component include cellulose powder, zeolites, talc, clay, alumina, kaolin, titania, calcium carbonate, barium sulfate, and the like, and zeolite and kaolin, which are excellent in the dispersibility in water, are especially preferable.

As to the size of (A) component used, it is preferable that an average particle size of the primary granules is 20 $\mu$m or less, from the viewpoint of the homogeneity of the distribution in the inner portion of the enzyme granules. In addition, the average particle size of the primary granules of (A) component is more preferably 10 $\mu$m or less, particularly preferably from 0.1 to 5 $\mu$m, from the viewpoints that the smaller the average particle size of the primary granules, the more compressed the enzyme granules become, so that the granule strength is improved owing to the compression, and thereby the dust generating property can be suppressed.

The content of (A) component in the enzyme granules is preferably 45% by weight or more of the enzyme granules, from the viewpoints of suppressing the generation of powdery dusts, giving breakdown and dispersibility in the enzyme granules, and promoting rapid elution of the enzyme, and the content is more preferably 50% by weight or more, from the viewpoint of further enhancing the fast dissolubility. On the other hand, the content is preferably 90% by weight or less, more preferably 80% by weight or less, particularly preferably 70% by weight or less, of the enzyme granules, from the viewpoints of suppressing the amount of dusts generated and preventing insoluble remnants. Therefore, in consideration of satisfying the fast dissolubility and the low dust generating property at the same time and preventing insoluble remnants, the content is preferably from 45 to 90% by weight or more, more preferably from 50 to 90% by weight, still more preferably from 50 to 80% by weight, particularly preferably from 50 to 70% by weight, of the enzyme granules.

In addition, in the present invention, (A) component may be each used alone, or in combination of both substances. Also, in a case where two or more kinds of (A) component are used in combination, the structure of the enzyme granules can be compressed or reinforced by formulating granules having different particle sizes or particles having different morphologies, whereby the dust generating property can be suppressed.

For instance, in a case where granules having an average particle size of the primary granules of from 2 to 3 $\mu$m are used in combination with granules having an average particle size of the primary granules of 1 $\mu$m or less, the suppression of dust generation can be achieved, as compared to a case where granules having an average particle size of the primary granules of from 2 to 3 $\mu$m are used alone. As described above, in a case where granules having different particle sizes are used in combination, although the proportion of the granules having smaller particle sizes is not particularly limited, the proportion is preferably from 5 to 60% by weight, more preferably from 5 to 50% by weight, of (A) component, from the viewpoint of an effect of suppression of dust generation.

2. (B) Component

The water-soluble binder of (B) component usable in the present invention is not particularly limited, as long as the substance is capable of binding the components constituting the granules themselves, the substance capable of exhibiting properties of having substantially no deactivation of an enzyme and being rapidly dissolving in water. Examples thereof include polyethylene glycols, polypropylene glycols, polyoxyethylene alkyl ethers and their derivatives, polyvinyl alcohols and their derivatives, water-soluble cellulose derivatives (the derivatives thereof include ether compounds, and the like), carboxylate polymers, starches, saccharides, and the like. The carboxylate polymers and the saccharides are preferable from the viewpoints of the productivity and the fast dissolubility, and salts of acrylic acid-maleic acid copolymers and polyacrylates are more preferable. The salts are preferably sodium salts, potassium salts and ammonium salts. Here, the molecular weight of the carboxylate polymer is preferably from 1,000 to 100,000, more preferably from 2,000 to 80,000.

The content of (B) component in the enzyme granules is preferably 5% by weight or more, more preferably 15% by weight or more, of the enzyme granules, from the viewpoint of the low dust generating property. The content is preferably 40% by weight or less, more preferably 30% by weight or less, of the enzyme granules, from the viewpoint of the fast dissolubility. Therefore, from the viewpoints of the low dust generating property and the fast dissolubility, the content is preferably from 5 to 40% by weight, more preferably from 15 to 30% by weight, of the enzyme granules.

In addition, the water-soluble binders used in the present invention can be formulated in combination of two or more kinds as occasion demands. A compound effect can be expected by combining water-soluble binders having two or more kinds of different effects. For instance, the stability of the enzyme granules can be further imparted by using a binder having stabilization ability of the enzyme in combination with a binder capable of rapidly dissolving in water.

3. (C) Component

The enzyme of (C) component usable in the present invention is not particularly limited, as long as the enzyme is capable of exhibiting such effects as detergency, when formulated in a detergent. For instance, there can be preferably used one or more kinds selected from cellulase, protease, pectinase, amylase, lipase, and dextranase.

The content of the enzyme in the enzyme granules is preferably 0.5% by weight or more, more preferably 2% by weight or more, from the viewpoint of the exhibition of an enzyme activity. The content is preferably 30% by weight or less, more preferably 25% by weight or less, from the viewpoint of the fast dissolubility. Therefore, from the viewpoints of the exhibition of an enzyme activity and the fast dissolubility, the content is preferably from 0.5 to 30% by weight, more preferably from 2 to 25% by weight.

As the form of the enzyme used, for instance, the enzyme may be used in the form of a concentrate prepared by filtering a culture comprising an enzyme produced by a microorganism and concentrating the culture, or in the form of an enzyme powder obtained by drying the concentrate. When an enzyme concentrate is used, the saccharides, inorganic salts, and the like, which cannot be separated by filtration may be contained in the concentrate.

4. (D) Component

The dye of (D) component usable in the present invention is not particularly limited, as long as the dye has high dissolubility. The higher the stability against heat, the more preferable, in a case where a process requiring heat, such as spray-drying, is employed. Concrete examples thereof are Red No. 106, Red No. 227, Blue No. 1, Blue No. 2, Green No. 3, Yellow No. 203, and the like. The content of these dyes is preferably 0.001% by weight or more of the enzyme granules, from the viewpoint of the coloring ability, and the content is preferably 1.0% by weight or less of the enzyme granules, from the viewpoint of the dispersibility of the dye. More preferably, the content is from 0.01 to 0.5% by weight of the enzyme granules. In addition, in the present invention, two or more kinds of dyes may be used in admixture. The adjustment of hue can be readily achieved by mixing two or more kinds of dyes.

5. Other Water-Soluble Substances

The enzyme granules of the present invention may comprise other water-soluble substances, besides (A) component, (B) component, and (C) component mentioned above, as occasion demands. For instance, there can be formulated as a stabilizing agent or an excipient, sodium chloride, calcium chloride, magnesium chloride, sodium sulfate, and the like. The amount of the other water-soluble substance is preferably such that a total sum of the contents of the enzyme, the water-soluble binder and the water-soluble substances is in a range of not exceeding 55% by weight of the enzyme granules. Especially, from the viewpoint of the fast dissolubility and the low dust generating property, the content of the other water-soluble substances is preferably 15% by weight or less, more preferably 10% by weight or less, of the enzyme granules.

A preferable combination of (A) component, (B) component, and the other water-soluble substances includes, for instance, zeolite as (A) component, a sodium polyacrylate and a saccharide as (B) components, and an excipient sodium sulfate as the other water-soluble substances.

6. Enzyme Granules of Present Invention

There are two embodiments for the enzyme granules of the present invention in accordance with the ranges of their average particle sizes. The enzyme granules of Embodiment 1 of the present invention have an average particle size of from 150 to 500 $\mu$m, and in order to suitably satisfy the fast dissolubility, the low dust generating property and the non-classifiable property, the average particle size is preferably from 200 to 400 $\mu$m. The average particle size may be adjusted, for instance, by sieving and separating the enzyme granules after preparation.

The average particle size of the enzyme granules of Embodiment 2 of the present invention is not particularly limited, because the optimal particle size varies depending upon the average particle size of the targeted enzyme granule aggregate. The average particle size is preferably 500 $\mu$m or less, more preferably 300 $\mu$m or less, from the viewpoint of the fast dissolubility. In addition, the average particle size is preferably 100 $\mu$m or more, more preferably 150 $\mu$m or more, from the viewpoint of the suppression of dust generation. Therefore, from the viewpoints of the fast dissolubility and the suppression of dust generation, the average particle size is preferably from 100 to 500 $\mu$m, more preferably from 100 to 300 $\mu$m, particularly preferably from 150 to 300 $\mu$m.

In addition, the enzyme granules comprising granules having a size of from 125 to 710 $\mu$m in an amount of 80% by weight or more are preferable, and those enzyme granules comprising such particles in an amount of 90% by weight or more of the entire granules are preferable, from the viewpoints of the dust generating property and the dissolubility. Further, from the viewpoint of the non-classifiable property, it is preferable that the particle size distribution is as homogeneous as possible.

Also, the bulk density of the enzyme granules is preferably from 500 to 1000 g/L or more, from the viewpoint of the non-classifiable property. The water content value of the enzyme granules in the present invention is preferably 10% by weight or less, more preferably 5% by weight or less, from the viewpoint of quality.

The enzyme granules of the present invention have a structure such that more amount of the water-soluble binder of (B) component is present near the surface of the enzyme granules than in the inner portion thereof. Since the water-soluble binder is localized near the surface as described above, the water-soluble binder is firstly dissolved in water, and thereafter water contacts with (A) component, so that the granules themselves undergo breakdown and disperse in water, whereby the enzyme in water is rapidly eluted. Therefore, as long as the enzyme granules have the above structure, the enzyme can be rapidly eluted even when the particle size or the bulk density becomes large, so that the insoluble remnants would be little. In addition, since the amount of the binder capable of binding the components constituting the granules themselves is large near the surface of the enzyme granules, the granule strength is further improved, whereby the low dust generating property can be realized.

The localized structure of the water-soluble binder can be confirmed by the following method.

First, there are prepared enzyme granules to be measured and a pulverized product of enzyme granules prepared by sufficiently pulverizing the enzyme granules in an agate mortar or the like, to be in a homogeneous state. Thereafter, the structures of both the enzyme granules and the pulverized product of enzyme granules are measured by a combined method of Fourier transform infrared spectroscopy (FT-IR) and photoacoustic spectroscopy (PAS) [referred to as "FT-IR/PAS"], under the conditions that information up to a depth of about 10 μm from the surface of the enzyme granules and the pulverized product of enzyme granules is obtained. In a case where the amount of the water-soluble binder of the former is greater than the amount of the water-soluble binder of the latter, the enzyme granules to be measured have a structure such that more amount of the water-soluble binder is present near the surface of the enzyme granules than in the inner portion thereof.

The measurement conditions for obtaining information up to a depth of about 10 μm from the surface of the enzyme granules and the pulverized product of enzyme granules include, for instance, resolution of 8 $cm^{-1}$, scanning speed of 0.63 cm/s, and 128 scans. The measurement device used includes, for instance, an infrared spectrometer "Model FTS-60A/896" manufactured by Bio-Rad Laboratories, and the PAS cell includes an acoustic detector "Model 300" manufactured by MTEC Corporation. Incidentally, "FT-IR/PAS" is described in *"APPLIED SPECTROSCOPY* 47, 1311–1316 (1993).

As mentioned above, the enzyme granules of the present invention are useful because the enzyme rapidly elutes with no insoluble remnants, the generation of powdery dusts is suppressed, and the granules exhibit non-classifiable ability.

In addition, the enzyme granules are preferably colored with a dye, from the viewpoint of obtaining acceptable appearance. The enzyme granules obtainable by spray-drying the slurry comprising a dye have a structure such that more amount of the dye is present near the surface of the enzyme granules than in the inner portion thereof. The enzyme granules having this structure are more vivid than those having a structure such that the dye is substantially homogenously dispersed in the entire granules, and this structure can be confirmed by slicing the enzyme granules, and observing its cross section.

7. Process for Preparing Enzyme Granules of Present Invention

It is desired that the process for preparing the enzyme granules of the present invention is, for instance, a process comprising spray-drying a slurry comprising (A) component, (B) component and (C) component, in order to prevent the lowering of the dissolubility owing to the compression of the enzyme granules. In addition, in order to obtain granules having a structure such that more amount of the water-soluble binder is present near the surface of the enzyme granules than in the inner portion thereof, there are, for instance, a process comprising preparing granules by drying the above slurry, and thereafter surface-coating the granule surface with a water-soluble binder; a process comprising spray-drying the above slurry, and the like. Especially, during heating and drying, since more amount of the water-soluble binder is collected near the surface of the granules along with the migration of water, a spray-drying process capable of easily obtaining granules having the above-mentioned structure is preferable.

When the enzyme granules of the present invention are prepared by spray-drying process, first, a slurry comprising each of the components is prepared. The content of each of the components for the resulting enzyme granules corresponds to the content of each of the components in the solid ingredients of the slurry. In the present specification, the term "solid ingredients" refers to (A) component, (B) component, (C) component, and other water-soluble substances.

In addition, as a dispersion medium for the preparation of the slurry, water is usually used.

It is preferable to increase the content of the solid ingredients of the slurry for spray-drying, because the dust generating property of the resulting enzyme granules can be lowered. In consideration of satisfying both the fast dissolubility and the low dust generation, the content of the solid ingredients is preferably 40% by weight or more, more preferably 50% by weight or more, of the slurry. In addition, from the viewpoint of ease in slurry spraying, the content of the solid ingredients is preferably 60% by weight or less. Therefore, the content of the solid ingredients is preferably from 40 to 60% by weight, more preferably from 50 to 60% by weight, of the slurry.

The order of formulation of (A) component, (B) component, and (C) component when the spray-dried slurry is prepared is not particularly limited. Since there is an optimal order from the viewpoints of the adjustment of slurry formulation and the dust generating property and such an order differs depending upon the properties of the formulated substances, an order can be appropriately optimized. For instance, in a case where zeolite is used as (A) component, a sodium polyacrylate and a saccharide are used as (B) components, and sodium sulfate is used as an excipient, it is preferable to formulate in the order of an enzyme, sodium sulfate, a saccharide, zeolite, and a sodium polyacrylate.

The prepared slurry is fed to a spray-drying device. The temperature for the slurry during feeding is preferably a temperature such that an enzyme is not substantially deactivated. From the viewpoints of the stability of the enzyme and the ease in the preparation of the slurry, the temperature is preferably from 10° to 40° C., more preferably from 20° to 30° C.

The air-blow temperature during spray-drying is preferably from 120° to 220° C., more preferably from 140° to 180° C. It is preferable to carry out spray-drying in this temperature range, because the productivity becomes excellent, and the enzyme is not substantially deactivated.

In addition, in the enzyme granules of Embodiment 1, for the purposes of decreasing the amount of dusts generated and improving the storage stability of the enzyme granules obtained by spray-drying, the surface of the above granules may be coated by using a coating agent comprising components which do not lose the dissolubility of the above granules. The coating agent includes water-soluble, thermoplastic substances, and concrete examples are polyethylene glycols and their derivatives, fatty acids, and the like (derivatives include ether compounds and the like). Especially, the polyethylene glycols and their derivatives are preferable, and those having a molecular weight of from 2000 to 10000 or so are more preferable.

A concrete coating operation includes, for instance, an embodiment of heat-fusing these coating agents, and coating and depositing on the surface of the spray-dried granules.

The enzyme granules of the present invention may be colored. The process for coloring the enzyme granules is not particularly limited, and it is preferable to use a dye rather than a pigment, from the viewpoints of suppressing dye-transfer to components other than the enzyme granules and to the granules, and staining ability to garments, and the like.

A process for coloring with a dye includes, for instance, a process comprising coating enzyme granules with a coating agent comprising a dye dispersed therein, to give colored enzyme granules; a process comprising spraying an aqueous solution prepared by dispersing a dye and a coating agent in enzyme granules to coat the granules, with subjecting the enzyme granules to fluidization and drying, to give colored enzyme granules; and a process comprising drying a slurry comprising (A) a water-insoluble substance and/or water-slightly soluble substance, (B) a water-soluble binder, (C) an enzyme, and (D) a dye, to give colored enzyme granules. Among them, a process comprising drying the slurry, to give colored enzyme granules, is preferable. In this process, since the dye is formulated in the slurry, the dye can be easily and homogeneously dispersed in the slurry, and as a result, granules having high coloring ability of the dye can be obtained. A process comprising spray-drying the slurry comprising a dye at a temperature in which the enzyme is not substantially deactivated, to give colored enzyme granules is especially preferable. By this process, the resulting granules have a structure such that more amounts of the water-soluble binder and the dye are present near the surface thereof. Therefore, the dye-transfer to components other than the enzyme granules or to the granules can be suppressed by this process, whereby enzyme granules having more excellent coloring ability can be obtained.

8. Enzyme Granule Aggregate

The enzyme granule aggregate comprising the enzyme granules may have a structure such that the enzyme granules are aggregated, and its process for aggregation is not limited. From the viewpoints of the stability of the aggregated structure and the productivity, an enzyme granule aggregate in which the enzyme granules are aggregated by a binder [hereinafter referred to as "(E) component] is preferable.

This enzyme granule aggregate comprises a structure such that several to several dozens of enzyme granules are bound to each other, with retaining the original shape and structure of the enzyme granules. Since the enzyme granules are aggregated without being compressed, the enzyme granules undergo breakdown and disperse in water as in the case of a single enzyme granule, whereby the enzyme in water is rapidly eluted, without losing the fast dissolubility owned by the enzyme granules. In addition, since the improvement in particle sizes is caused by aggregation, the dust generating property owned by the enzyme granules can be further suppressed.

The average particle size of the enzyme granule aggregate is preferably 150 $\mu$m or more, more preferably 200 $\mu$m or more, particularly preferably 300 $\mu$m or more, from the viewpoint of the visual confirmability. Also, the average particle size is preferably 2000 $\mu$m or less, more preferably 1000 $\mu$m or less, particularly preferably 700 $\mu$m or less, from the viewpoint of the suppression of classification. Therefore, from the viewpoints of the visual confirmability and the suppression of classification, the average particle size is preferably from 150 to 2000 $\mu$m, more preferably from 200 to 1000 $\mu$m, still more preferably from 300 to 1000 $\mu$m, particularly preferably from 300 to 700 $\mu$m.

The average particle size of the enzyme granule aggregate can be controlled by the average particle size of the enzyme granules and the conditions for aggregation. For instance, if the average particle size of the enzyme granules is made small under the same aggregation conditions, the average particle size of the enzyme granule aggregate becomes small. In addition, when the enzyme granules having the same average particle size are used, if the forming rate of aggregation is increased, the average particle size of the enzyme granule aggregate becomes large.

Likewise, the bulk density can be also controlled by the average particle size of the enzyme granules and the conditions for aggregation. For instance, granules having a low bulk density can be obtained by making the particle size of the enzyme granules small and loosely aggregating the enzyme granules.

From the above, as to the classification during blending the enzyme granule aggregate in the detergent composition, the classification can be suppressed by controlling the average particle size and the bulk density of the aggregate. For instance, such an enzyme granule aggregate can be widely formulated, for instance, from detergent compositions having a low bulk density such as conventional detergents to detergent compositions having a high bulk density such as compact-type detergents.

The shape of the enzyme granule aggregate is not particularly limited. For instance, the classification in the detergent can be further suppressed by having an irregular shape.

In order that the enzyme granule aggregate has a fast dissolubility, the enzyme granules themselves must have fast dissolubility. In addition, since the dust generating property of the enzyme granule aggregate is highly influenced by the generated dusts of the enzyme granules, it is desirable that the dust generating property of the enzyme granules is suppressed as much as possible.

When the enzyme granules are aggregated by (E) component in the present invention, (E) component is not particularly limited as long as it has an ability of binding the enzyme granules with each other and does not substantially deactivate an enzyme. (E) component may be the same one as that for (B) component, or those other than (B) component or (B) component which is present in more amount near the surface of the enzyme granules may be used. In addition, (E) component may be water-insoluble or water-soluble, and two or more kinds may be used in combination.

It is preferable that at least one kind of (E) component is water-soluble, from the viewpoint of the fast dissolubility. In addition, when only water-insoluble (E) component is used, it is preferable that (E) component easily allows penetration of water into the surface of the enzyme granules in water, without completely coating the surface of the enzyme granules, from the viewpoint of the fast dissolubility.

The water-insoluble (E) component includes, for instance, fatty acids, higher alcohols, cured oils, and the like. The water-soluble (E) component includes, for instance, polyethylene glycols, polypropylene glycols, polyoxyethylene alkyl ethers and derivatives thereof, polyvinyl alcohols and derivatives thereof, polyvinyl pyrrolidones, water-soluble cellulose derivatives (their derivatives include ether compounds, and the like), carboxylate polymers, starches, saccharides, and the like. The polyethylene glycols and their derivatives are preferable, from the viewpoints of the fast dissolubility and the low dust generating property. The polyethylene glycols have a molecular weight of preferably from 3000 to 30000, and more preferably from 5000 to 15000.

Also, the enzyme granule aggregate may further comprise other substances as occasion demands, besides the enzyme granules and (E) component mentioned above. The other substances contained in the enzyme granule aggregate are not particularly limited, as long as the fast dissolubility of the enzyme granule aggregate is not lost. The enzyme granule aggregate may be used in combination of two or more kinds. For instance, for the purpose of adjusting a bulk density, there can be formulated sodium chloride, calcium chloride, magnesium chloride, sodium sulfate, and the like.

9. Process for Preparing Enzyme Granule Aggregate

A process for preparing an enzyme granule aggregate include (1) a process comprising adding water or an aqueous solution containing (E) component to the enzyme granules of Embodiment 2, and drying and/or cooling the mixture, to give an enzyme granule aggregate; (2) a process comprising adding a molten thermoplastic (E) component to the enzyme granules, and cooling the mixture, to give an enzyme granule aggregate; and the like. The process (1) is preferable, from the viewpoints of the fast dissolubility and the productivity.

Among the process (1), embodiments for adding water are:

(i) a process comprising spraying water with drying the enzyme granules, thereby partially dissolving (B) component on the surface of the enzyme granules to deposit and aggregate thereon, and thereafter further drying the product;

(ii) a process in a case where enzyme granules are prepared by spray-drying a slurry, comprising stopping drying of the enzyme granules at a water content of 10% by weight or more, thereafter partially dissolving (B) component on the surface of the enzyme granules by such steps as allowing to stand or fluidizing the enzyme granules, depositing and aggregating the enzyme granules, and thereafter drying the aggregate; and the like.

Among the process (1), an embodiment for adding an aqueous solution containing (E) component includes:

(iii) a process comprising spraying (E) component in the form of an aqueous solution with drying enzyme granules, thereby depositing and aggregating with (B) component on the enzyme granule surface partially dissolved with the aqueous solution, and sprayed (E) component, and thereafter further drying and/or cooling the product; and the like. The process of (iii) is preferable, from the viewpoints of the suppression of dust generation and the particle size control.

The process (2) includes:

(iv) a process comprising spraying a molten thermoplastic (E) component with fluidizing the enzyme granules, depositing these components on the enzyme granule surface, solidifying (E) component by cooling, and aggregating the granules; and the like.

The aggregation operation is not particularly limited, as long as the enzyme granules are deposited and aggregated with suppressing the compression of the enzyme granules. The aggregation operation includes, for instance, a process comprising depositing and aggregating by allowing to stand the granules or by fluidizing the granules. Among them, the deposition and aggregation by fluidizing the granules are preferable, from the viewpoints of the particle size control and the productivity.

The process for fluidization includes, for instance, a process of fluidizing by an agitation and tumbling granulator, or by a fluidized bed, and the like. From the viewpoint of the particle size control, the process by the fluidized bed is preferable.

Therefore, as the process for preparing an enzyme granule aggregate, a process comprising spraying (E) component in the form of an aqueous solution with fluidizing and drying the enzyme granules, thereby depositing and aggregating (B) component on the surface of the enzyme granules partially dissolved with an aqueous solution, and the sprayed (E) component, and thereafter further drying the aggregate, is preferable, from the viewpoint of the suppression of dust generated, the particle size control, and the productivity. A process comprising spraying (E) component in the form of an aqueous solution with fluidizing and drying the enzyme granules by using a fluidized bed, thereby depositing and aggregating (B) component on the surface of the enzyme granules partially dissolved with an aqueous solution, and the sprayed (E) component, and thereafter further drying the aggregate, is more preferable, from the viewpoints of the suppression of the dusts generated and the particle size control.

When the enzyme granule aggregate is prepared by the above process (1), the drying temperature is not particularly limited, as long as it is a temperature where the enzyme is not substantially deactivated. The higher the drying temperature, the better, from the viewpoint of the productivity, and the drying temperature is preferably 30° C. or more, preferably 50° C. or more. On the other hand, the lower the drying temperature, the better, from the viewpoint of the enzyme activity, and the drying temperature is 100° C. or less, more preferably 70° C. or less. Therefore, the drying temperature is preferably from 30° to 100° C., more preferably from 50° to 70° C., from the viewpoints of the productivity and the enzyme activity.

In addition, when an enzyme granule aggregate is prepared by the above process (1), in a case where a thermoplastic substance such as a polyethylene glycol is selected as (E) component, it is preferable that drying is carried out at a melting temperature for (E) component or lower, from the viewpoint of the suppression of the deposition to the inner portion of the mixer.

(E) component usable for aggregation of the enzyme granules includes those listed in Section 8. above. In addition, the amount of (E) component added is not particularly limited, and it may not be added when (B) is used therefor, and the like. When (E) component is added, the amount may be preferably 20% by weight or less, more preferably 10% by weight or less, particularly preferably 5% by weight or less, of the enzyme granule aggregate, from the viewpoint of the fast dissolubility. On the other hand, the amount is preferably 1% by weight or more, more preferably 3% by weight or more, from the viewpoint of the low dust generating property. Therefore, the amount is preferably from 1 to 20% by weight, more preferably from 1 to 10% by weight, still more preferably from 3 to 5% by weight, of the enzyme granule aggregate, from the viewpoints of the fast dissolubility and the low dust generating property. In addition, when (E) component is used in the form of an aqueous solution, (E) component may be water-soluble or water-insoluble. It is preferable that (E) component is dissolved or homogeneously dispersed, from the viewpoint of the dispersibility in the enzyme granules. The concentration of (E) component is preferably from 5 to 60% by weight, more preferably from 10 to 50% by weight, from the viewpoint of the dispersibility in the enzyme granules.

10. Coloring of Enzyme Granule Aggregate

The enzyme granule aggregate may be colored. It is preferable to use a dye rather than a pigment from the viewpoints of suppressing dye-transfer to components other than the enzyme granule aggregate and to the granules, and suppressing staining ability to garments, and the like.

The process for coloring with a dye includes, for instance, a process comprising depositing and aggregating the granules using (E) component comprising a dye dispersed therein, to give colored enzyme granule aggregate; a process comprising spraying an aqueous solution prepared by dispersing a dye and (E) component to coat the granules, with subjecting the enzyme granules to fluidization and drying, to give a colored enzyme granule aggregate; and a process of preparing enzyme granules prepared by drying a slurry comprising (A) component, (B) component and (C) component, the process comprising formulating a dye in a slurry, and coloring the enzyme granules, thereby giving a colored enzyme granule aggregate. The process comprising drying a slurry formulated with a dye, and coloring the enzyme, thereby giving a colored enzyme granule aggregate, is preferable. In this process, since the dye is formulated in a slurry, the dye can be easily homogenously dispersed in the slurry, and consequently, the granules having high coloring ability of the dye can be obtained. A process comprising spray-drying a slurry comprising a dye at a temperature where the enzyme is not substantially deactivated, and coloring the enzyme granules, to give a colored enzyme granule aggregate, is particularly preferable. By this process, the resulting enzyme granules and the enzyme granule aggregate have a structure such that more amounts of the water-soluble binder and the dye are present near the surface thereof. Therefore, the dye-transfer to the components other than the enzyme granule aggregate and the granules is suppressed by this process, whereby an enzyme granule aggregate having more excellent coloring ability can be obtained.

The usable dye is not particularly limited, as long as it is a substance having a high dissolubility in water. The dye may be any ones, and in a case where the dye is used in a preparation process requiring heat such as spray-drying, those having high stability against heat are preferable. As the dye, there can be used Red No. 106, Red No. 227, Blue No. 1, Blue No. 2, Green No. 3, Yellow No. 203, and the like. The amount of the dye formulated is preferably 0.01% by weight or more to the enzyme granules, from the viewpoint of the coloring ability. In addition, the amount is preferably 1.0% by weight or less, more preferably from 0.001 to 0.5% by weight or less, of the enzyme granules, from the viewpoint of the dispersibility of the dye.

In addition, in the present invention, two or more kinds of dyes may be used. The hue can be easily adjusted by mixing two or more kinds of dyes.

The fast dissolubility, the low dust generating property, the average particle size, the bulk density, the non-classifiable property, and the staining ability in the present invention are measured by the following methods.

[Fast Dissolubility]

In the present invention, the term "enzyme granules having fast dissolubility" refers to those enzyme granules having an elution rate of 70% or more and a dissolution rate of 85% or more. The elution rate corresponds to a time period until an enzyme is eluted from the enzyme granules to exhibit their performance, and the dissolution rate corresponds to a degree of prevention of insoluble remnants, respectively. The enzyme granules satisfying the fast dissolubility are very highly preferable because the enzymes rapidly act and at the same time there are no insoluble remnants.

The elution rate of an enzyme was calculated as follows. A 100 mL beaker (inner diameter: 105 mm) was charged with 100 mg of enzyme granules, and 100 mL of water at 20° C. having a water hardness of 4° DH was poured thereinto. The mixture was stirred with a magnetic stirrer (length: 35 mm, diameter: 8 mm) (200 r.p.m.), to give an enzyme solution. The value calculated by the equation (1) was defined as an elution rate of the enzyme for this enzyme solution.

$$\text{Elution Rate } (\%) = \frac{[A \times 100]}{B} \qquad (1)$$

wherein A: an enzyme activity value for the enzyme solution obtained by stirring under above stirring conditions for 30 seconds; and B: an enzyme activity value indicating a constant value when the an enzyme activity value for the enzyme solution was assayed with the passage of time under above stirring conditions.

Incidentally, as to the assay for the enzyme activity value, an assay suitable for each enzyme may be employed.

For instance, in the case of a cellulase, the following CMC activity assay can be employed. To a substrate solution comprising 0.4 mL of an aqueous solution of 2.5% by weight carboxymethyl cellulose (CMC), 0.2 mL of 0.5 M glycine buffer (pH 9.0), and 0.3 mL of deionized water was added 0.1 mL of an enzyme solution, and mixed, and the resulting liquid mixture was incubated at 40° C. for 20 minutes. Next, the deoxy saccharide was quantified by utilizing the following 3,5-dinitrosalicylic acid (DNS) method. Specifically, 1 mL of a DNS reagent was added to 1 mL of the liquid mixture after incubation, and the liquid mixture was heated at 100° C. for 5 minutes. Subsequently, after cooling the liquid mixture, 4 mL of deionized water was added thereto to dilute the solution. Thereafter, the absorbance was determined at 535 nm to quantify the deoxy saccharide. In the case of assaying under these conditions, an amount of an enzyme capable of releasing 1 μmol of a deoxy saccharide, calculated on the basis of glucose, in one minute is defined as one unit.

In addition, in the case of a protease, the following casein method can be employed. One milliliter of 50 mM borate-sodium hydroxide buffer (pH 10.0) containing 1% by weight of casein was mixed with 0.1 mL of an enzyme solution, and the liquid mixture was incubated at 40° C. for 10 minutes. Next, 2 mL of a reaction-stopper solution (0.123 M trichloroacetic acid-0.246 M sodium acetate-0.369 M acetic acid) was added to this liquid mixture, and the mixture was incubated at 30° C. for 20 minutes. Subsequently, the resulting liquid was filtered using a filter paper (manufactured by Whatman, No. 2), and the protein degradation product in the filtrate was assayed by improved Folin-Loewy method. In the case of assaying under these conditions, an amount of an enzyme capable of releasing 1 mmol of tyrosine in one minute was defined as one unit.

The dissolution rate of the enzyme granules was calculated as follows.

A 1 L beaker (inner diameter: 105 mm) was charged with 1 L of water at 5° C. having a water hardness of 4°DH, and 1 g of enzyme granules were added thereto. The mixture was stirred with a magnetic stirrer (length: 35 mm, diameter: 8 mm) (800 r.p.m.) for 60 seconds. The value calculated by the equation (2) was defined as a dissolution rate of the enzyme granules for the resulting aqueous solution.

$$\text{Dissolution Rate } (\%) = \left\{1 - \frac{D}{C}\right\} \times 100 \qquad (2)$$

wherein C: weight (g) of the enzyme granules supplied; and
D: dry weight (g) of enzyme granules remaining on a sieve after sieving the aqueous solution obtained under the above stirring conditions using a standard sieve (sieve-opening: 74 μm) according to JIS Z 8801 [drying conditions: keeping at a temperature of 105° C. for one hour, and thereafter keeping in a desiccator (25° C.) containing a silica gel therein for 30 minutes].

[Low Dust Generating Property]

The term "low dust generating property" in the present invention refers to those having an amount of dusts generated of 1000 mg or less. The lower the amount of dusts generated, the more desirable, and the amount of dusts generated is more preferably 500 mg or less, still more preferably 100 mg or less. In addition, the standard value for the amount of dusts generated also varies depending upon the kinds of the enzymes. For instance, it is preferable that the amount of dusts generated, such as protease which greatly affects the human bodies, is preferably 100 mg or less, more preferably 20 mg or less.

Here, the term "amount of dusts generated" is assayed as follows. With rotating the pulverization balls at a rotational speed of 44 r.p.m., 20 g of the enzyme granules were placed in a rotatable dustmeter capable of passing a dry air at 20 L/min from an air introducing inlet 4 to an air discharging outlet 5 and capturing in a filter 3 granules carried along the air flow in the upper convergent part, the rotatable dustmeter comprising a cylinder having a diameter of 6.0 cm of which upper end was converged and 4 pulverization balls 1 incorporated therein each having a diameter of 2.0 cm and a weight of 32.2 g. The amount of dusts generated is defined as an amount of powdery dusts when carrying out a 20 minutes determination therewith. As the filter 3, one having a diameter of 5.0 cm, a size of captured particles of 0.5 μm, and a pressure loss of 0.42 kPa when an air flow rate was 5 cm/s was used.

The rotatable dustmeter used for the determination is not particularly limited. As this dustmeter, a rotatable dustmeter having such a structure as shown in FIG. 1, for instance, one made commercially available by Heubach GmbH, Dustmeter TYPE. III, can be used.

[Average Particle Size]

The average particle size was measured by vibrating each of standard sieves according to JIS Z 8801 for 5 minutes, and calculating the size from a weight percentage depending upon the sieve-openings of the sieves.

[Bulk Density]

The bulk density was measured by a method according to JIS K 3362.

[Non-Classifiable Property]

In Examples 1 to 6 and Comparative Example 1, the following operations were carried out.

One gram of the colored enzyme granules were blended with 100 g of detergent granules (average particle size: 400 μm, bulk density: 750 g/L), and thereafter vibration was applied to the mixture with a mixer. Whether or not classification was generated was determined visually.

In Examples 7 to 15 and Comparative Examples 2 and 3, the following operations were carried out.

Six grams of the colored enzyme granules were blended with 594 g of a detergent composition (average particle size: 400 μm, bulk density: 750 g/L), and thereafter the mixture was packed in a container (length: 9 cm, width: 15 cm, and height: 11 cm) and then sealed. The sealed container was loaded on a carrier of a truck, and transported for 1000 km. Thereafter, the seal was opened, and the presence or absence of classification generation was determined visually.

[Staining Ability]

The amount 0.1 g of the colored enzyme granules were blended with 10 g of detergent granules (average particle size: 400 μm, bulk density: 750 g/L). A test cloth (25×16 cm) was spread over a vat, and water at 20° C. having water hardness of 4°DH was poured into the vat until the test cloth was soaked. Next, the blend of the enzyme granules and the detergent granules was evenly sprinkled on the test cloth. A separate test cloth was further overlaid on the test cloth, and water was further poured gently to a level where an entire cloth was soaked. Thereafter, it was allowed to stand overnight, with maintaining the room temperature at 30° C. After rinsing the test cloth, the test cloth was press-dried. Whether or not stained garment was generated on the dried test cloth was determined visually. As the test cloths, those made of the polyester and cotton were used.

EXAMPLE 1

A spray-dried slurry having a content of solid ingredients of 45% by weight was prepared from the raw materials shown in Table 1 and water. The spray-dried slurry was sprayed at a spraying pressure of 2.5 MPa using a pressure-type spray nozzle. The slurry was spray-dried by using a counter current spray-drying tower (diameter: 3 m, tower height: 10 m) at an air-blow rate of 100 m³/min, an air-blow temperature of 150° C., a slurry spraying rate of 200 kg/Hr. From the resulting granules, the granules having a size of 1410 μm or more were removed using a sieve, to give enzyme granules having a water content value of 4.1% by weight.

TABLE 1

| | Composition (% by weight) | | | | |
|---|---|---|---|---|---|
| | Example 1 | Example 2 | Example 3 | Example 4 | Comp. Ex. 1 |
| (A) | | | | | |
| Zeolite*4 | 70 | 35 | 65 | 30 | 39.5 |
| Kaolin*5 | — | 35 | — | 30 | — |

TABLE 1-continued

| | Composition (% by weight) | | | | |
|---|---|---|---|---|---|
| | Example 1 | Example 2 | Example 3 | Example 4 | Comp. Ex. 1 |
| (B) | | | | | |
| Sodium Polyacrylate*1 | — | — | — | 15 | 11 |
| Sodium Polyacrylate*2 | 12 | 12 | — | — | — |
| Sodium Salt of Acrylic Acid-Maleic Acid Copolymer*3 | — | — | 12.5 | — | — |
| Saccharide | 12 | 12 | 12.5 | — | 11 |
| (C) | | | | | |
| Cellulase | 6 | 6 | 4 | — | 5.5 |
| Protease | — | — | — | 20 | — |
| Other Water-Soluble Substance | | | | | |
| Sodium Sulfate | — | — | 6 | 5 | 33 |

*1 Completely neutralized product, molecular weight: 10000
*2 Completely neutralized product, molecular weight: 20000
*3 Degree of neutralization: 0.8, molecular weight: 30000
*4 Average primary particle size: 3.0 μm
*5 Average primary particle size: 0.4 μm Incidentally, in Table 1, "Cellulase" is an alkali cellulase disclosed in Japanese Patent Laid-Open No. Hei 6-343461, and "Protease" is ALKALI PROTEASE K-16 disclosed in Japanese Patent Laid-Open No. Hei 5-25492. As the saccharide, Maltorich ("MR-25" manufactured by Showa Sangyo Kabushiki Kaisha) was used.

EXAMPLE 2

A spray-dried slurry having a content of solid ingredients of 45% by weight was prepared from the raw materials shown in Table 1 and water. The slurry was subjected to spray-drying and sieving under the same conditions as in Example 1, to give enzyme granules having a water content value of 4.5% by weight.

EXAMPLE 3

A spray-dried slurry having a content of solid ingredients of 55% by weight was prepared from the raw materials shown in Table 1 and water. The slurry was subjected to spray-drying and sieving under the same conditions as in Example 1, to give enzyme granules having a water content value of 3.4% by weight.

EXAMPLE 4

A spray-dried slurry having a content of solid ingredients of 50% by weight was prepared from the raw materials shown in Table 1 and water. The slurry was subjected to spray-drying under the same conditions as in Example 1. Subsequently, granules having a size of 125 μm or less and granules having a size of 710 μm or more were removed using a sieve, to give enzyme granules having a water content value of 3.8% by weight.

EXAMPLE 5

In an agitation and tumbling granulator (High-Speed Mixer manufactured by Fukae Powtec Corp., Model "FS-10") of which jacket warm water at 60° C. flowed through were supplied 5.0 kg of the enzyme granules obtained in Example 4, and stirred at a rotational speed of the main axis of 240 r.p.m., and a rotational speed of disintegrating impellers at 2700 r.p.m. With stirring, 250 g of a polyethylene glycol (molecular weight: 6000) melted at 80° C. was supplied as a coating agent. After supplying the coating agent, the mixture was stirred for 10 minutes to allow surface coating of the granules. From the resulting granules, granules having a size of 1410 μm or more were removed using a sieve, to give enzyme granules having a water content value of 3.1% by weight.

Figure 2:
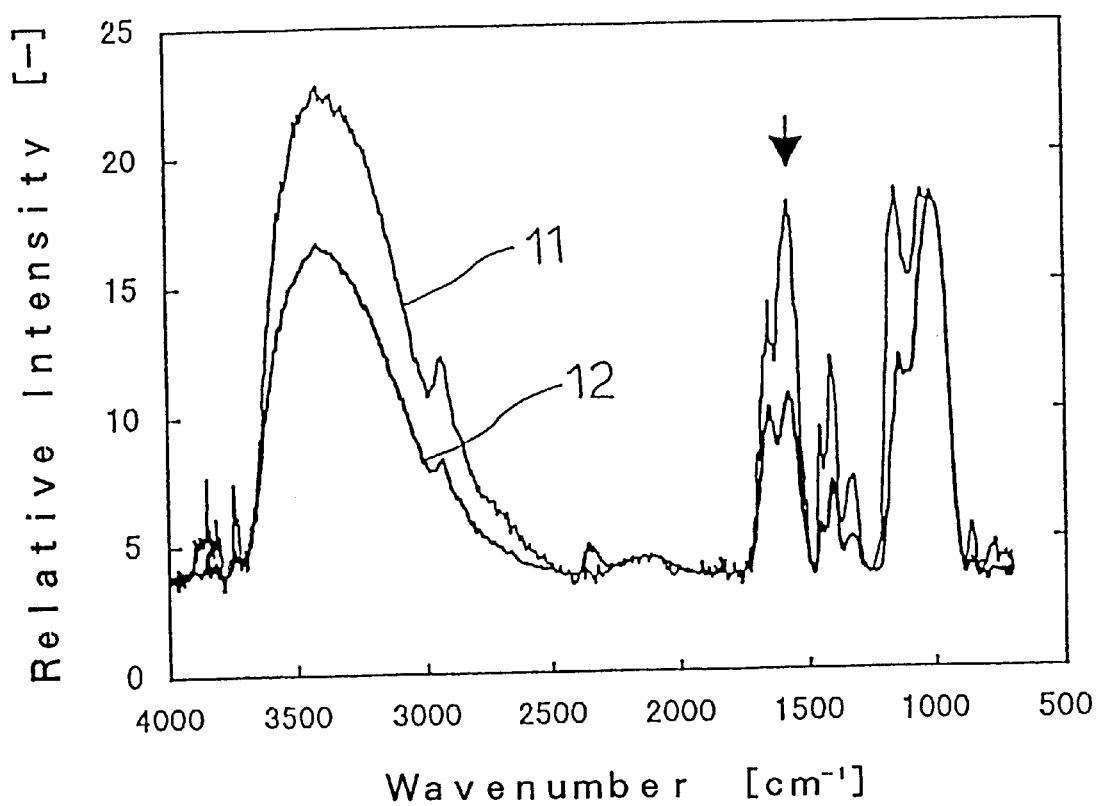
FIG. 2 is a graph showing the measurement results obtained by FT-IR/PAS of the enzyme granules obtained in Example 3. An arrow in the figure indicates the position of a peak for the water-soluble binder. 11 is data for those near the surface of the granules, and 12 is data for those in the inner portion thereof.

The elution rate, the dissolution rate, the average particle size, the bulk density, the amount of dusts generated, and the non-classifiable property of the enzyme granules obtained in Example 1 to 5 are shown in Table 2. All of these granules satisfied the required properties, and the enzyme granules were excellent in the fast dissolubility, the suppression of the amount of dusts generated, and the non-classifiable property. As a result of measuring each of these enzyme granules in accordance with the FT-IR/PAS described above, it was confirmed that all of these enzyme granules have localized structure such that the water-soluble binder exists more near the surface than in the inner portion thereof. FIG. 2 shows the measurement results for the enzyme granules obtained in Example 3 in accordance with FT-IR/PAS.

COMPARATIVE EXAMPLE 1

A spray-dried slurry having a content of solid ingredients of 55% by weight was prepared from the raw materials shown in Table 1 and water. The slurry was subjected to spray-drying and sieving under the same conditions as in Example 1, to give enzyme granules having a water content value of 4.3% by weight. The elution rate, the dissolution rate, the average particle size, the bulk density, the amount of dusts generated, and the non-classifiable property of the resulting enzyme granules are shown in Table 2.

EXAMPLE 6

A slurry was prepared by formulating 0.2 parts by weight of a dye Blue No. 1, based on 100 parts by weight of the solid ingredients of the slurry, in the composition of Example 1 during the preparation of the slurry. The slurry was subjected to spray-drying and sieving under the same conditions as in Example 1, to give enzyme granules which were uniformly colored in blue. The elution rate, the dissolution rate, the average particle size, the bulk density, the amount of dusts generated, and the non-classifiable property of the resulting enzyme granules were substantially the same as those of the enzyme granules in Example 1. No staining ability was observed in the enzyme granules. In addition, the enzyme granules were formulated in a detergent composition, and the dye-transfer was examined. As a result, no dye-transfer was found in the enzyme granules.

TABLE 2

|  | Example 1 | Example 2 | Example 3 | Example 4 | Example 5 | Comparative Example 1 |
|---|---|---|---|---|---|---|
| Elution Rate (%) | 98.5 | 95.4 | 91.1 | 100.0 | 97.7 | 98.5 |
| Dissolution Rate (%) | 99.6 | 99.0 | 98.0 | 99.7 | 99.1 | 99.8 |
| Average Particle Size ($\mu$m) | 164 | 169 | 246 | 204 | 207 | 271 |
| Bulk Density (g/L) | 757 | 921 | 779 | 830 | 801 | 562 |
| Amount of Dusts Generated (mg) | 493.0 | 146.7 | 133.9 | 62.0 | 13.0 | 1286.8 |
| Presence of Classification Generation (Non-Classifiable Property) | None | None | None | None | None | None |

EXAMPLE 7

A spray-dried slurry having a content of solid ingredients of 55% by weight was prepared from the raw materials shown in Table 3 and water. The spray-dried slurry was sprayed at a spraying pressure of 2.5 MPa using a pressure-type spray nozzle. The slurry was spray-dried by using a counter current spray-drying tower (diameter: 3 m, tower height: 10 m) at an air-blow rate of 100 m$^3$/min, an air-blow temperature of 150° C., a slurry spraying rate of 200 kg/Hr. From the resulting granules, the granules having a size of 1410 $\mu$m or more were removed using a sieve, to give enzyme granules having a water content value of 4.2% by weight.

With fluidizing and drying 0.96 kg of the enzyme granules in a fluidized bed (bottom area: 0.19 m$^2$ and tower height: 1 m) at an air-blow rate of 60 m$^3$/Hr and an air-blow temperature of 60° C., 200 g of water was sprayed from an upper powder layer at a rate of 15 g/min. After termination of spraying, the granules were dried for 10 minutes, to give an enzyme granule aggregate. Incidentally, in Table 3, "Cellulase" is an alkali cellulase disclosed in Japanese Patent Laid-Open No. Hei 6-343461, and "Protease" is ALKALI PROTEASE K-16 disclosed in Japanese Patent Laid-Open No. Hei 5-25492. As the saccharide, Maltorich ("MR-25" manufactured by Showa Sangyo Kabushiki Kaisha) was used.

EXAMPLE 8 with fluidizing and drying 0.96 kg of the enzyme granules of Example 7 using a fluidizing bed (the same apparatus and the same conditions), an aqueous solution prepared by dissolving 40 g of a polyethylene glycol (molecular weight: 6000) in 160 g of water was sprayed from an upper powder layer at a rate of 15 g/min. After the termination of spraying, the granules were dried for 10 minutes, and then cooled to ordinary temperature, to give an enzyme granule aggregate.

EXAMPLE 9

With fluidizing 0.96 kg of the enzyme granules of Example 7 using a fluidizing bed (the same apparatus and the same conditions), a liquid in a melting state prepared by heating 40 g of a polyethylene glycol (molecular weight: 6000) to 80° C. was sprayed from an upper powder layer at a rate of 3 g/min. After the termination of spraying, the granules were cooled to ordinary temperature, to give an enzyme granule aggregate.

EXAMPLE 10

A spray-dried slurry having a content of solid ingredients of 50% by weight was prepared from the raw materials shown in Table 3 and water. The slurry was spray-dried under the same conditions as in Example 7, except that a slurry spraying rate was 180 kg/Hr. Subsequently, granules having a size of 1410 $\mu$m or more were removed using a sieve, to give enzyme granules having a water content value of 4.5% by weight.

With fluidizing and drying 0.95 kg of the resulting enzyme granules using a fluidizing bed (bottom area: 0.19 m$^2$ and tower height: 1 m) at an air-blow rate of 60 m$^3$/Hr and an air-blow temperature of 60° C., an aqueous solution prepared by dissolving 50 g of a polyethylene glycol (molecular weight: 6000) in 117 g of water was sprayed from a bottom powder layer at a rate of 10 g/min. After the termination of spraying, the granules were dried for 10 minutes, to give an enzyme granule aggregate.

EXAMPLE 11

A spray-dried slurry having a content of solid ingredients of 45% by weight was prepared from the raw materials shown in Table 3 and water. The slurry was spray-dried under the same conditions as in Example 7, except that a slurry spraying rate was 160 kg/Hr. Subsequently, granules having a size of 1410 $\mu$m or more were removed using a sieve, to give enzyme granules having a water content value of 3.4% by weight.

With fluidizing and drying 0.95 kg of the resulting enzyme granules using a fluidizing bed (bottom area: 0.19 m$^2$ and tower height: 1 m) at an air-blow rate of 60 m$^3$/Hr and an air-blow temperature of 60° C., an aqueous solution prepared by dissolving 50 g of a polyethylene glycol (molecular weight: 6000) in 200 g of water was sprayed from an upper powder layer at a rate of 15 g/min. After the termination of spraying, the granules were dried for 10 minutes, to give an enzyme granule aggregate.

EXAMPLE 12

A spray-dried slurry having a content of solid ingredients of 55% by weight was prepared from the raw materials shown in Table 3 and water, and the slurry was spray-dried under the same conditions as in Example 7. Subsequently, granules having a size of 1410 $\mu$m or more were removed using a sieve, to give enzyme granules having a water content value of 4.3% by weight.

With fluidizing and drying 0.95 kg of the resulting enzyme granules using a fluidizing bed (bottom area: 0.19 m$^2$ and tower height: 1 m) at an air-blow rate of 60 m$^3$/Hr and an air-blow temperature of 60° C., an aqueous solution prepared by dissolving 50 g of a polyethylene glycol (molecular weight: 6000) in 117 g of water was sprayed from a bottom powder layer at a rate of 10 g/min. After the termination of spraying, the granules were dried for 10 minutes, to give an enzyme granule aggregate.

TABLE 3

| | Composition (% by weight) | | |
|---|---|---|---|
| | Examples 7–9 | Examples 10–11 | Example 12 |
| (A) | | | |
| Zeolite*[1] | 70 | 60 | 39.5 |
| (B) | | | |
| Sodium Polyacrylate*[2] | — | 15 | 11 |
| Sodium Polyacrylate*[3] | 12 | — | — |
| Saccharide | 12 | — | 11 |
| (C) | | | |
| Cellulase | 6 | — | 5.5 |
| Protease | — | 20 | — |
| Other Water-Soluble Substance | | | |
| Sodium Sulfate | — | 5 | 33 |

*[1]Average primary particle size: 3.0 μm
*[2]Completely neutralized product, molecular weight: 10000
*[3]Completely neutralized product, molecular weight: 20000

Figure 3:
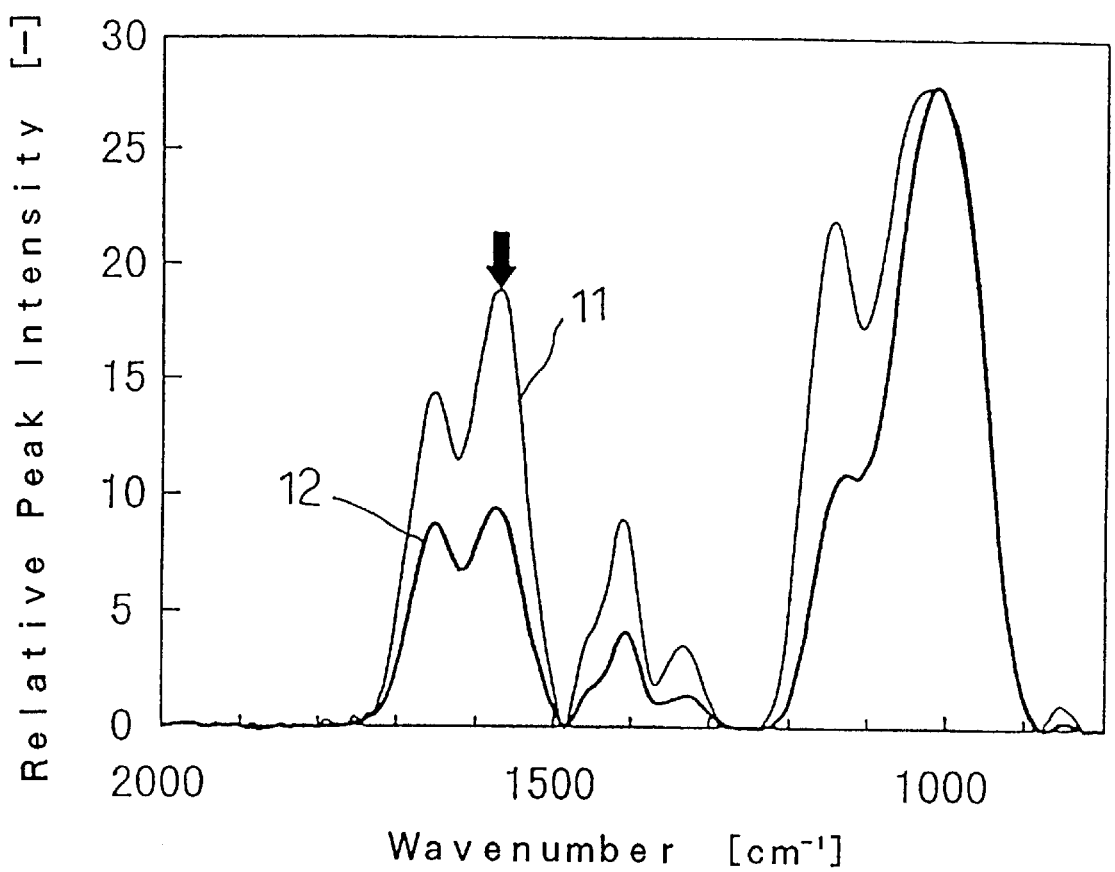
FIG. 3 is a graph showing the measurement results obtained by FT-IR/PAS of the enzyme granules obtained in Example 10. An arrow in the figure indicates the position of a peak for the water-soluble binder. 11 is data for those near the surface of the granules, and 12 is data for those in the inner portion thereof.

The elution rate, the dissolution rate, the average particle size, the bulk density, the amount of dusts generated, and the non-classifiable property of the enzyme granule aggregates obtained in Examples 7 to 12 are shown in Table 4. The inventive products were enzyme granule aggregates excellent in the fast dissolubility, suppression of the amount of dusts generated, and the non-classifiable property. As a result of measuring each of these enzyme granules in accordance with FT-IR/PAS described above, it was confirmed that all of these enzyme granules have localized structure such that (B) component exists more near the surface than in the inner portion thereof. FIG. 3 shows the measurement results for the enzyme granules obtained in Example 10 in accordance with FT-IR/PAS.

EXAMPLE 13

The elution rate, the dissolution rate, the average particle size, the bulk density, the amount of dusts generated, and the non-classifiable property of the enzyme granules obtained in Example 7 before aggregation are shown in Table 4.

EXAMPLE 14

The elution rate, the dissolution rate, the average particle size, the bulk density, the amount of dusts generated, and the non-classifiable property of the enzyme granules obtained in Example 10 before aggregation are shown in Table 4.

COMPARATIVE EXAMPLE 2

The elution rate, the dissolution rate, the average particle size, the bulk density, the amount of dusts generated, and the non-classifiable property of the enzyme granules obtained in Example 11 before aggregation are shown in Table 4.

COMPARATIVE EXAMPLE 3

The elution rate, the dissolution rate, the average particle size, the bulk density, the amount of dusts generated, and the non-classifiable property of the enzyme granules obtained in Example 12 before aggregation are shown in Table 4.

TABLE 4

| | Examples | | | | | | | | Comparative Examples | |
|---|---|---|---|---|---|---|---|---|---|---|
| | 7 | 8 | 9 | 10 | 11 | 12 | 13 | 14 | 2 | 3 |
| Elution Rate (%) | 97.3 | 95.2 | 96.5 | 98.2 | 97.5 | 98.5 | 98.4 | 99.0 | 99.2 | 98.5 |
| Dissolution Rate (%) | 99.2 | 99.3 | 99.0 | 99.7 | 99.2 | 99.0 | 99.8 | 99.8 | 99.8 | 99.8 |
| Average Particle Size (μm) | 398 | 402 | 432 | 384 | 310 | 395 | 252 | 246 | 141 | 271 |
| Bulk Density (g/L) | 566 | 552 | 537 | 608 | 595 | 505 | 716 | 775 | 803 | 562 |
| Amount of Dusts Generated (mg) | 106 | 51 | 72 | 42 | 292 | 475 | 279 | 255 | 1503 | 1287 |
| Presence of Classification Generation | None | None | None | None | None | None | None | None | Present | None |

EXAMPLE 15

A slurry was prepared by formulating 0.1 parts by weight of a dye Blue No. 1, based on 100 parts by weight of the solid ingredients of the slurry, in the composition of Example 8 during the preparation of the slurry. The slurry was subjected to spray-drying and aggregation operation under the same conditions as in Example 8, to give an enzyme granule aggregate which was uniformly colored in blue. The elution rate, the dissolution rate, of the average particle size, the bulk density, the amount of dusts generated, and the non-classifiable property of the resulting enzyme granule aggregate were substantially the same as those of the enzyme granule aggregate in Example 8. No staining ability was observed in the enzyme granules. In addition, the enzyme granule aggregate was formulated in a detergent composition, and the dye-transfer was examined. As a result, no dye-transfer was also found in the enzyme granule aggregate.

INDUSTRIAL APPLICABILITY

According to the present invention, there is provided enzyme granules which exhibit such effects as the fast dissolubility, the suppression of dust generation, and non-classifiable ability. Further, according to the present invention, when the enzyme granules are colored with a dye, there can be provided enzyme granules with suppressed staining ability against fibers and suppressed dye-transfer against detergent granules. Further, according to the present invention, there is provided an enzyme granule aggregate which exhibits such effects as the fast dissolubility, the suppression of dust generation, and non-classifiable ability.

EQUIVALENT

Those skilled in the art will recognize, or be able to ascertain using simple routine experimentation, many equivalents to the specific embodiments of the invention described in the present specification. Such equivalents are intended to be encompassed in the scope of the present invention described in the following claims.

What is claimed is:

1. Enzyme granules comprising (A) a water-insoluble substance and/or a slightly water-soluble substance; (B) a water-soluble binder; and (C) an enzyme, wherein the content of said (A) component is 45% by weight or more, and wherein the enzyme granules have an average particle size of from 150 to 500 µm and a bulk density of from 500 to 1,000 g/L, and have a structure such that more amount of said (B) component is present near the surface of the enzyme granules than in the inner portion thereof.

2. The enzyme granules according to claim 1, wherein the content of (B) component is from 5 to 40% by weight.

3. The enzyme granules according to claim 1, which are colored with a dye.

4. The enzyme granules according to claim 3, wherein more amount of dye is present near the surface of the enzyme granules than in the inner portion thereof.

5. A process for preparing the enzyme granules of claim 1, comprising spray-drying a slurry comprising (A) the water-insoluble substance and/or a slightly water-soluble substance; (B) the water-soluble binder; and (C) the enzyme at a temperature so as not to substantially deactivate the enzyme, to give the enzyme granules.

6. A process for preparing the enzyme granules of claim 3, comprising spray-drying a slurry comprising (A) the water-insoluble substance and/or a slightly water-soluble substance; (B) the water-soluble binder; (C) the enzyme; and (D) the dye at a temperature so as not to substantially deactivate the enzyme, to give the enzyme granules.

7. The process according to claim 5, wherein the content of solid ingredients in the slurry is from 40 to 60% by weight.

* * * * *